(12) United States Patent
Hakky

(10) Patent No.: US 11,278,410 B2
(45) Date of Patent: Mar. 22, 2022

(54) REAR-TIP EXTENDER FOR PENILE IMPLANT

(71) Applicant: Coloplast A/S, Humlebaek (DK)

(72) Inventor: Tariq Hakky, Johns Creek, GA (US)

(73) Assignee: Coloplast A/S, Humlebaek (DK)

( * ) Notice: Subject to any disclaimer, the term of this patent is extended or adjusted under 35 U.S.C. 154(b) by 104 days.

(21) Appl. No.: 16/817,625

(22) Filed: Mar. 13, 2020

(65) Prior Publication Data
US 2020/0289269 A1   Sep. 17, 2020

Related U.S. Application Data

(60) Provisional application No. 62/818,266, filed on Mar. 14, 2019.

(51) Int. Cl.
*A61F 2/26* (2006.01)

(52) U.S. Cl.
CPC ........ *A61F 2/26* (2013.01); *A61F 2230/0069* (2013.01); *A61F 2250/0007* (2013.01)

(58) Field of Classification Search
CPC ....... A61F 2/26; A61F 2250/0007; A61F 5/41
See application file for complete search history.

(56) References Cited

U.S. PATENT DOCUMENTS

| | | |
|---|---|---|
| 3,672,708 A | 6/1972 | Zemberry |
| 4,541,420 A * | 9/1985 | Timm ........................ A61F 2/26 600/40 |
| 4,600,223 A | 7/1986 | de Vries |
| 4,943,091 A | 7/1990 | Bartholomew |
| 5,010,882 A | 4/1991 | Polyak et al. |
| 5,088,477 A | 2/1992 | Subrini |
| 5,782,865 A | 7/1998 | Grotz |
| 6,575,987 B2 | 6/2003 | Gellman et al. |
| 6,808,489 B2 | 10/2004 | George et al. |
| 7,648,456 B2 | 1/2010 | Steele, Sr. |
| 7,976,457 B2 | 7/2011 | Steele, Sr. |
| 8,052,593 B2 | 11/2011 | Jahns et al. |
| 2003/0220539 A1 | 11/2003 | George et al. |
| 2012/0157764 A1 | 6/2012 | Borgaonkar et al. |
| 2015/0011823 A1 | 1/2015 | Terlecki |
| 2017/0087049 A1* | 3/2017 | Hutchison .............. A61H 19/44 |
| 2018/0214271 A1 | 8/2018 | Poucher et al. |

FOREIGN PATENT DOCUMENTS

| | | |
|---|---|---|
| EP | 0428314 B1 | 1/1997 |
| EP | 3028673 A1 | 6/2016 |
| GB | 2163354 A | 2/1986 |
| WO | 9707743 A1 | 3/1997 |
| WO | 2012025118 A1 | 3/2012 |

* cited by examiner

*Primary Examiner* — John P Lacyk
(74) *Attorney, Agent, or Firm* — Coloplast Corp., Coloplast A/S; Nick Baumann

(57) ABSTRACT

A device for extending a penile implant includes a support segment having a tip portion and a receiving segment coupled to a distal end of the penile implant. The receiving segment is configured to rotatably receive a threaded portion to secure the support segment to the penile implant. An extension segment is configured to at least partially surround the threaded portion to extend a length between the tip portion and the penile implant.

10 Claims, 3 Drawing Sheets

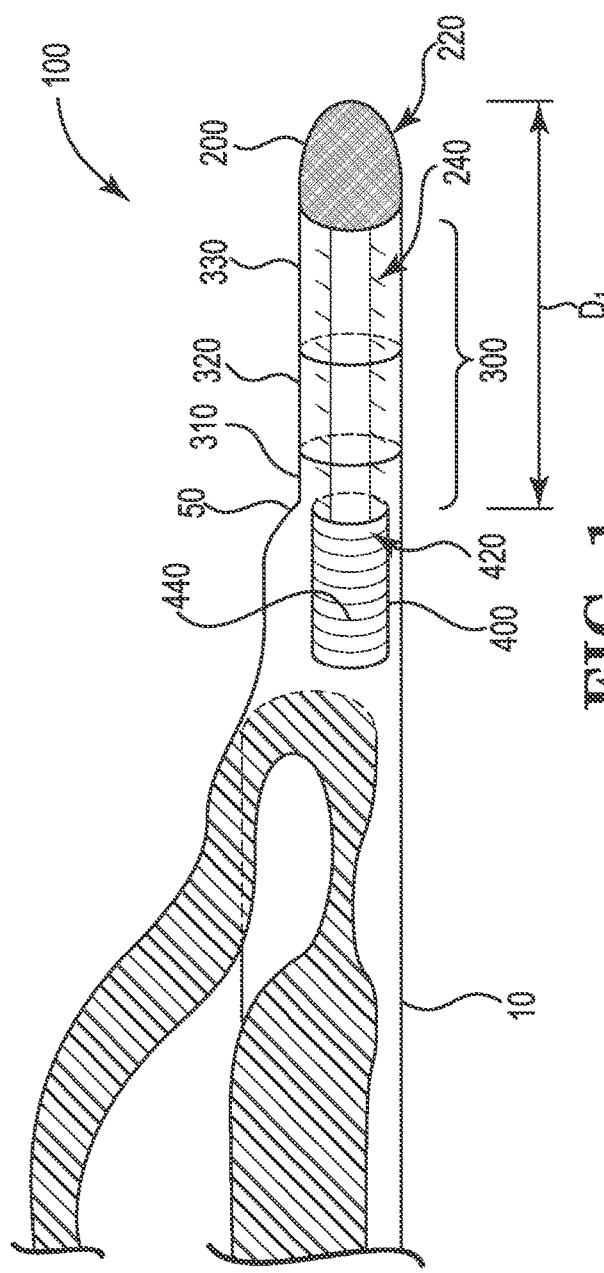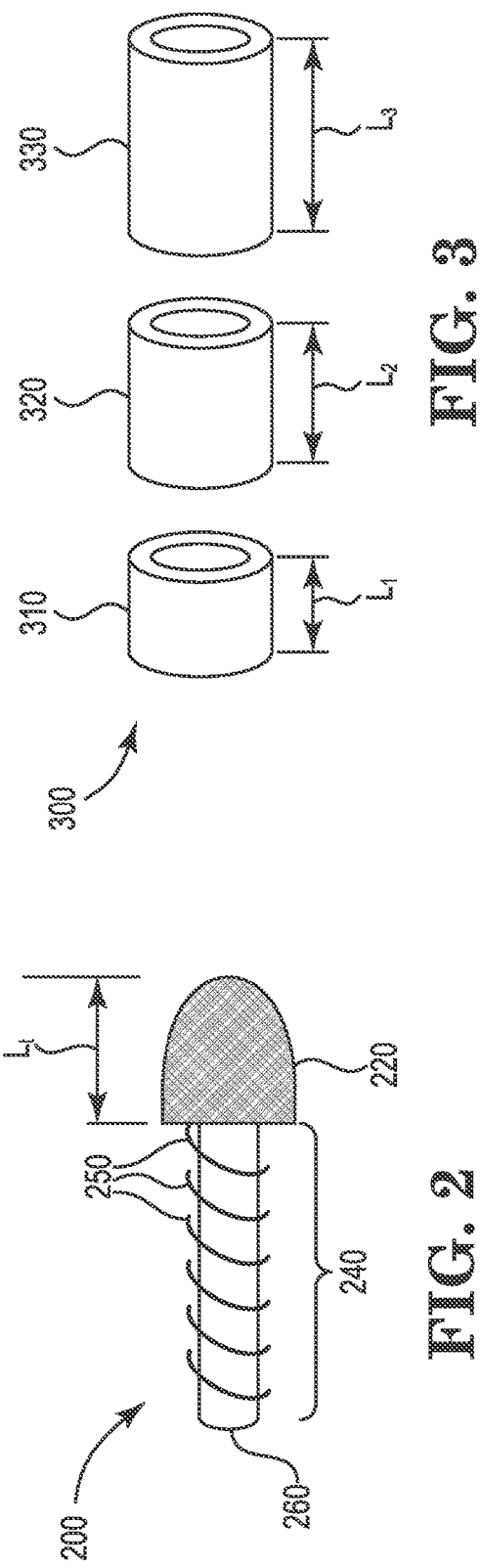

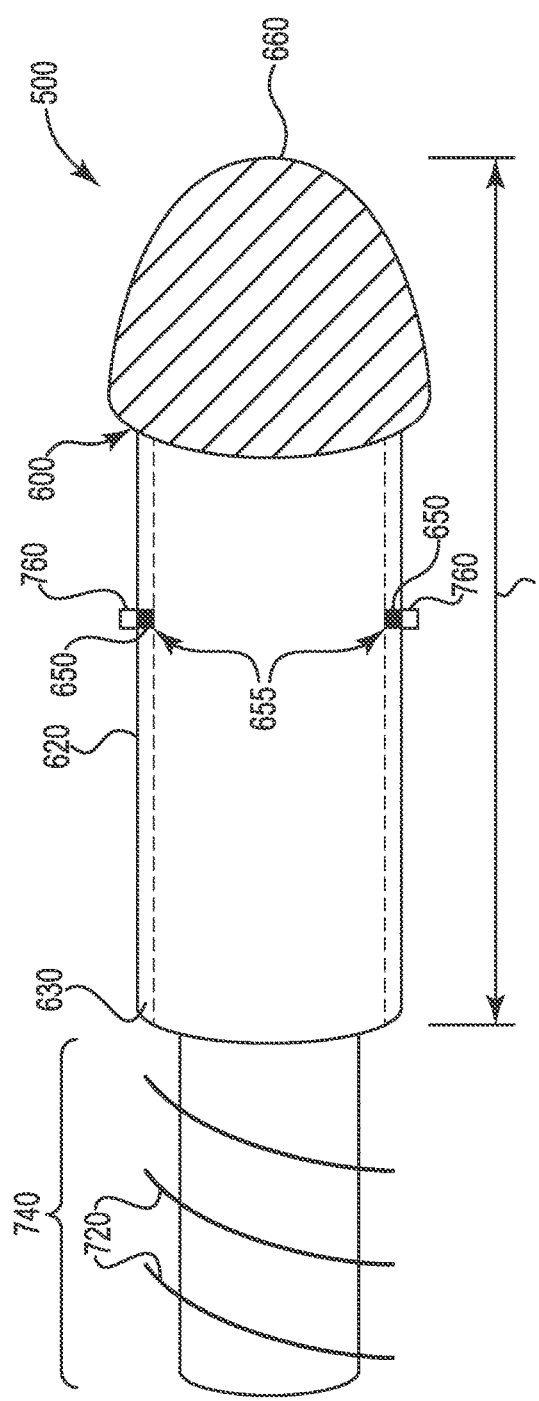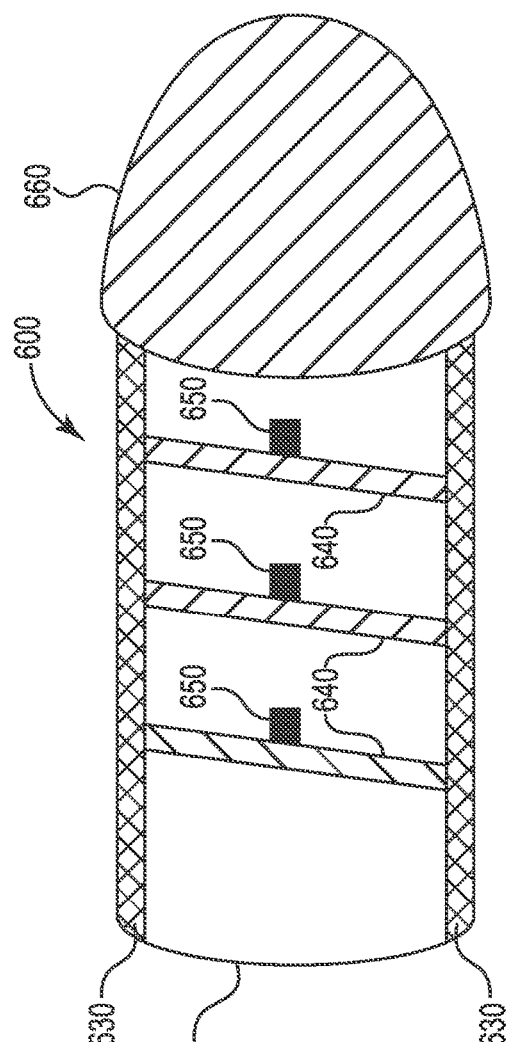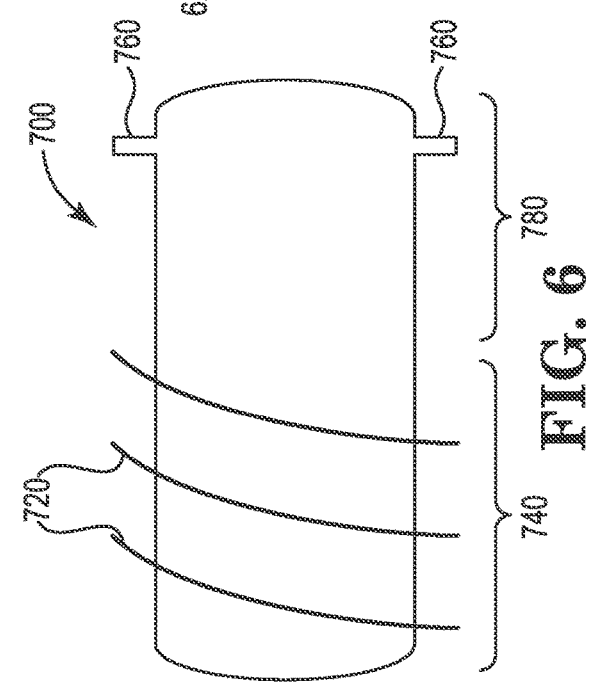

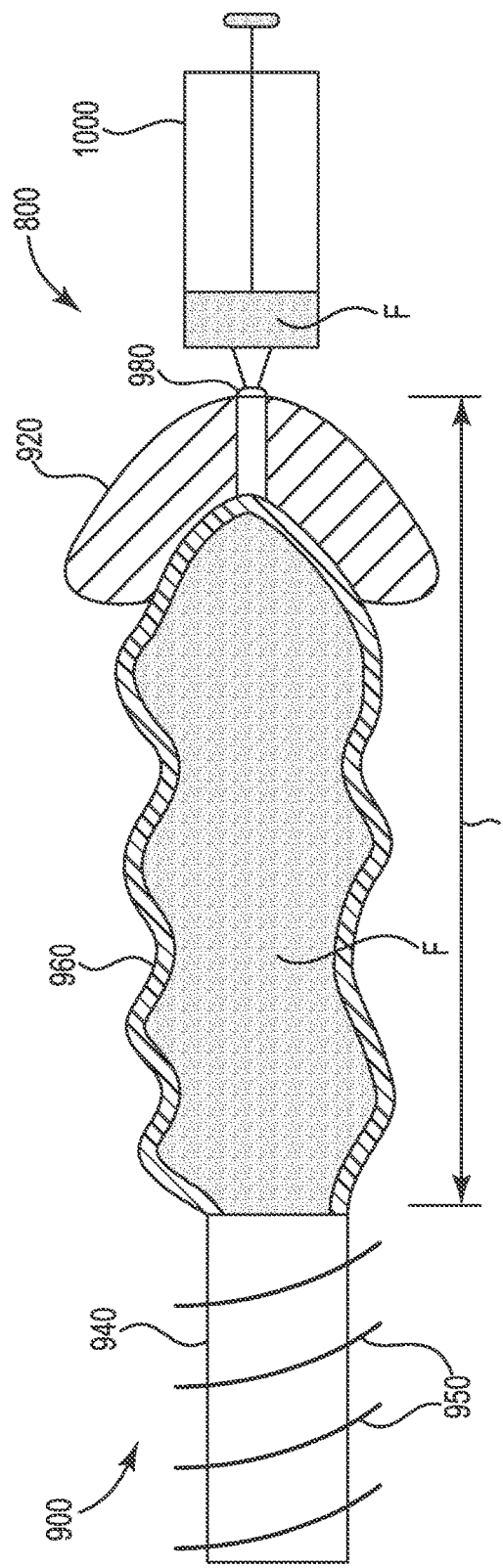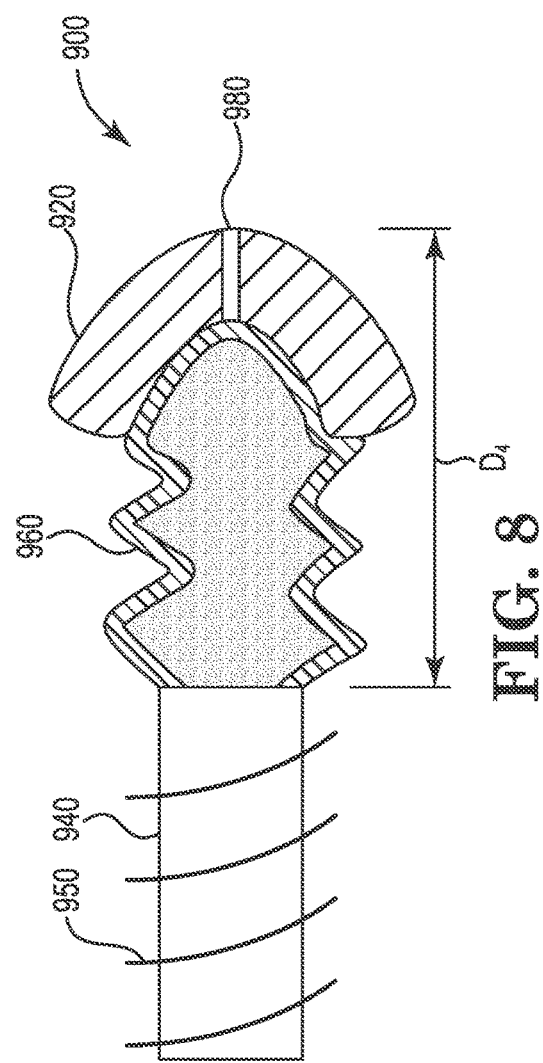

REAR-TIP EXTENDER FOR PENILE IMPLANT

BACKGROUND

Penile prostheses offer men suffering from erectile dysfunction with an erection that is suitable for penetrative intercourse. A variety of treatment options exist for erectile dysfunction patients including implants. Implants may include a self-contained, fluid-filled system and may include tip extenders to tailor implants to the appropriate sizing requirements and/or to assist with exit tubing angle. However, surgeons have found conventional hollow rear tip extenders (RTE) problematic in that they negatively affect axial loading and may be insecurely attached. A problem associated with hollow RTE's is that the pivot point, having the highest load, is moved anteriorly toward the head of the penis. As a result, portions of hollow RTE's have been known to snap off and cause penile instability during use causing discomfort and embarrassment to the patient. Therefore, an alternate RTE is desired.

SUMMARY

Various aspects of the present disclosure are directed toward devices, systems, and methods for extending of a penile implant prostheses. The devices, systems, and methods may include a support segment, a receiving segment, and at least one extension segment for securing the device at a desired extension distance to the penile implant prostheses. The support segment may have a tip portion and a threaded portion. The receiving segment may be coupled to a distal end of the penile implant. The receiving segment may be configured to rotatably receive the threaded portion to secure the support segment to the penile implant. The at least one extension segment may be configured to at least partially surround the threaded portion to extend a length between the tip portion and the penile implant. The at least one extension segment may comprise a plurality of extension segments. The plurality of extension segments may include a first extension segment of a first length and a second extension segment of a second length, wherein the first length is different from the second length. The first extension segment may be arranged at the distal end of penile implant and the second extension segment is arranged between the first extension segment and the tip portion. The plurality of extension segments may include three extension segments configured to at least partially surround the threaded portion. The tip portion may include a rounded shape contoured according to the distal end of the penile implant. The support segment may comprise a biopolymer material. The at least one extension segment may comprise a biopolymer material. The at least one extension segment may be substantially cylindrical.

Various aspects of the present disclosure are also directed toward devices, systems, and methods that may include an extension device including a bellows segment and a bevels segment. The bellows segment may have a hollow body portion and a rounded tip portion. The body portion may include a circumferential wall having a plurality of internal grooves and at least one aperture adjacent and perpendicular to the internal grooves. The bevels segment may have at least one protrusion configured to spirally rotate to engage with the plurality of internal grooves of the bellows segment and lock into place within the at least one aperture. The at least one aperture may include a pair of apertures disposed 180 degrees apart, the pair of apertures adjacent and perpendicular to the internal grooves. The circumferential wall may include at least two pairs of apertures offset longitudinally and configured to facilitate different desired extension distances. The rounded tip portion may include a shape contoured according to the distal end of the penile implant. The bellows segment may comprise a biopolymer material. The bevels segment may comprise a biopolymer material.

Various aspects of the present disclosure are also directed toward devices, systems, and methods that may include an extension device including a support segment having a tip portion, a threaded portion, and an expandable bellows segment. The expandable bellows segment is arranged between the tip portion and the threaded portion. The tip portion includes a port configured to receive a fluid for expanding the expandable bellows segment. The threaded portion is configured to mate with a receiving segment coupled to a distal end of the penile implant. The receiving segment may be configured to rotatably receive the threaded portion to secure the support segment to the penile implant. The expandable bellows segment may be configured to facilitate desired extension distances. The tip portion may include a rounded shape contoured according to the distal end of the penile implant. The support segment may comprise a biopolymer material. The support segment may be of one-piece construction.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 1 is a schematic view of a screw in adjustable rear tip extender device, according to some embodiments.

FIG. 2 illustrates a detailed view of the support member of FIG. 1.

FIG. 3 illustrates an exploded view of extension segments of FIG. 1.

FIG. 4 is a perspective view of click lock rear tip extender device, according to some embodiments.

FIG. 5 illustrates a detailed view of the bellows segment of FIG. 4.

FIG. 6 illustrates a cross-sectional view, rotated 90 degrees, of the bevels segment of FIG. 4.

FIG. 7 is a schematic view of another screw in adjustable rear tip extender device having an expandable bellows segment in an expanded configuration, according to some embodiments.

FIG. 8 illustrates the screw in adjustable rear tip extender as in FIG. 7 in an unexpanded configuration.

While the invention is amenable to various modifications and alternative forms, specific aspects have been shown by way of example in the drawings and are described in detail below. The intention, however, is not to limit the invention to the particular aspects described. On the contrary, the invention is intended to cover all modifications, equivalents, and alternatives falling within the scope of the invention as defined by the appended claims.

DESCRIPTION

Various aspects of the present disclosure are directed toward implantable medical devices for the treatment of male erectile dysfunction. Surgical implantation of prostheses may include penile implants. In certain implant procedures, the implant includes an extension device in order to appropriately size the device to the patient. The extension devices, consistent with various aspects of the present disclosure, may be capable of extending an implant for erectile dysfunction to the desired extension distance.

FIG. 1 illustrates an extension device 100, according to some embodiments. Device 100 is an adjustable rear tip extender device. As shown in FIG. 1, the device 100 includes a support segment 200, a plurality of extension segments 300, and a receiving segment 400 insertable within the distal end 50 of penile implant 10. Receiving segment 400 of device 100 may be a screw in feature for attachment of device 100 to the distal end 50 of a penile implant 10. The extension segments 300 may include an open central bore or area as shown.

As shown in FIG. 1, support segment 200 has a tip portion 220, an end portion 260 (shown in FIG. 2), and a threaded portion 240 between the tip portion 220 and the end portion 260. Tip portion 220 includes a rounded shape contoured according to the distal end 50 of the penile implant 10 so that the penile implant 10 and device 100 combination has a smooth external surface. The smooth external surface of the tip portion 220 allows device 100 to seamlessly take the place of the end (not shown) of the penile implant 10. The smooth design of tip portion 220 allows for easier insertion. Tip portion 220 is solid and thus the pivot point will not be altered by the addition of device 100 to penile implant 10, therefore, the stability of the penile implant 10 is uncompromised. As shown in FIG. 2, end portion 260 may be blunt, in other words, a smooth surface free of sharp corners or edges. Advantages of the smooth surface of the end portion 260 include ensuring injury-free insertion by the surgeon while also ensuring that the penile implant 10 will not be damaged during insertion.

The device 100 is adjustable to a desired extension distance $D_1$ according to the number and/or width of the extension segments 300 loaded onto the support segment 200. In other words, one, two, three, or more extension segments 300 may at least partially surround or encircle the support segment 200 in order to achieve a desired extension distance $D_1$. As shown in FIG. 3, each extension segment 300 may have a different length, e.g., segment 310 having a first length $L_1$, segment 320 having a second length $L_2$, segment 330 having a third length $L_3$. Therefore, the extension distance $D_1$ is adjustable according to whether the segment 310 and/or segment 320 and/or segment 330 is loaded onto the support segment 200. The device 100 may be used, for example, to provide a prosthesis having a desired length that is appropriate to the patient. In certain instances, additional hollow extension segments 300 than the ones shown may be included to further adjust the length as desired.

In some embodiments, the support segment 200 having tip portion 220 a tip length, $L_t$, contributes also to the extension distance $D_1$. In a non-limiting example, length $L_t$ contributes 0.5 cm to the extension distance $D_1$. Each segment adds as needed, e.g., in a non-limiting example, segment 310 having length $L_1$ of 0.5 cm, segment 320 having length $L_2$ of 1.0 cm, and segment 330 having length $L_3$ of 1.5 cm. Segments 310, 320, and 330 are added so that the extension distance $D_1$ ranges from about 0.5 cm including length $L_t$ only to about 3.5 cm with the three segments 310, 320, and 330 added. In some embodiments, any number of extension segments 300 (e.g., 310, 320, 330) are used as desired. In various embodiments, extension segments 300 may each be of the same width or of different widths as in the non-limiting example above.

As shown in FIG. 1, receiving segment 400 is disposed at the distal end 50 of the penile implant 10. Receiving segment 400 is coupled to the support segment 200 by rotating the support segment 200 into the receiving segment 400 to secure the device at a desired extension distance $D_1$. Threaded portion 240 includes a plurality of threads 250. Receiving segment 400 includes a hole 420, and the hole 420 including a plurality of internal grooves 440. Internal grooves 440 (shown in FIG. 1) are configured to matingly receive the plurality of the threads 250 (shown in FIG. 3) to secure the support segment 200 at the desired extension distance $D_1$.

Device 100 is attached to a penile implant 10 at the distal end 50 via receiving segment 400. Device 100 works by being screwed into the back of the penile implant 10. Moreover, device 100 includes the non-hollow support segment 200 to provide greater strength along the extension distance $D_1$. Device 100 may be advantageously safer and more stable than other RTE designs, which were hollow and prone to failure by snapping off due to the pivot point moving anteriorly toward the head of the penis.

Support segment 200 and/or extension segments 300 and/or receiving segment 400 of the device 100 may include any suitable medical grade material. Examples of such materials include various biopolymer, and/or other various biologically compatible materials. In preferred instances, the biopolymer material is hydrophilic. In certain instances, the support segment 200 may be Bioflex®. In certain instances, the extension segments 300 may be a Bioflex®. In certain instances, the receiving segment 400 may be a Bioflex. FIG. 4 illustrates an extension device 500, according to other embodiments. Device 500 may include a click lock rear tip extender device for extending a penile implant. The device 500 includes a bellows segment 600 and a bevels segment 700. As illustrated in the cross-sectional view of bellow segment 600 in FIG. 5, bellows segment 600 has a hollow body portion 620 and a rounded tip portion 660. In some embodiments, the rounded tip portion 660 includes a shape contoured according to the distal end of the penile implant. In some embodiments, the tip portion 660 may be solid.

As shown in FIG. 5, the hollow body portion 620 includes a circumferential wall 630 having a plurality of internal grooves 640. The circumferential wall 630 further includes at least one aperture 650 through the circumferential wall 630. The at least one aperture 650 is adjacent and perpendicular to an internal groove 640. In some embodiments, the at least one aperture 650 may include a shape, such as a circular or rectangular shape. In some embodiments, the circumferential wall 630 includes a pair of apertures 655 disposed 180 degrees apart (as shown in FIG. 4). Each of the apertures 650 in the pair of apertures 655 is adjacent and perpendicular to an internal groove 640. In yet other embodiments, the circumferential wall 630 includes at least two pairs of apertures 655 with each pair of apertures 655 offset longitudinally and configured to facilitate different desired extension distances $D_2$. As shown in FIG. 5, each aperture 650 is offset longitudinally. In various embodiments, circumferential wall 630 may include three pairs of apertures 655, or four pairs of apertures 655, or more, with each pair of apertures 655 offset longitudinally to allow adjusting the device 500 to a desired extension distances $D_2$.

As shown in FIGS. 4 and 6, bevels segment 700 includes a plurality of external bevels 720 in a first portion 740 for mating with a distal end of a penile implant (not shown). The bevels segment 700 includes at least one protrusion 760 in a second portion 780. The at least one protrusion 760 is spirally rotatable to engage with the plurality of internal grooves 640 of the bellows segment 600 and lock into place within the at least one aperture 650. The at least one protrusion 760 may be clicked or locked into place to the at least one aperture 650 when aligned at a desired extension distance $D_2$. In some embodiments, the at least one protrusion 760 may include a shape, such as a circular or rectangular shape, to matingly engage with the at least one aperture 650. In some embodiments, portion 780 includes a pair of protrusions 765, which may be clicked or locked into place to a pair of apertures 655 when aligned at a desired extension distance $D_2$.

In certain instances, the aperture(s) 650 may have dimensions different from the protrusion(s) 760 to facilitate a snap fit. In certain instances, the protrusion(s) 760 of bevels segment 700 are disengaged from the bellow segment 600 to adjust the distance $D_2$ and then reengaged by mating the protrusion(s) 760 to another longitudinally offset aperture 650 or pair of apertures 655.

Bellows segment 600 and/or bevels segment 700 of the device 500 may include any suitable medical grade material. Examples of such materials include various biopolymer, and/or other various biologically compatible materials. In certain instances, the bellows segment 600 may be Bioflex®. In certain instances, the bevels segment 700 may be a Bioflex®.

FIG. 7 illustrates an extension device 800, according to some embodiments. Device 800 is another adjustable rear tip extender device. As shown in FIG. 7, the device 800 includes a support segment 900 having a tip portion 920, a threaded portion 940, and an expandable bellows segment 960. Expandable bellows segment 960 is arranged between the tip portion 920 and the threaded portion 940. Expandable bellows segment 960 is hollow. Threaded portion 940 includes a plurality of threads 950.

As shown in FIG. 7, the tip portion 920 further includes a port 980 configured to receive a fluid F. Fluid F may include biomedically compatible fluids such as. Fluid F is injected into port 980 via a delivery apparatus 1000, which may be a syringe. As fluid F is injected or otherwise delivered into port 980, fluid F passes through tip 920 and is received by the expandable bellows segment 960. As fluid F is filled into the expandable bellows segment 960, into the expandable bellows segment 960 is elongated to expand longitudinally to a desired distance. Advantageously, device 800 is expandable to any desired distance from an initial unexpanded configuration $D_i$, having no fluid F in expandable bellows segment 960, to a final fully expanding configuration $D_f$, having expandable bellows segment 960 fully loaded with fluid F to maximum capacity. FIG. 7 shows expandable bellows segment 960 in an expanded configuration providing a desired distance $D_3$. Support segment 900 of FIG. 7 is shown in FIG. 8 in an unfilled, unexpanded configuration providing a distance $D_4$, wherein distance $D_3$ is less than distance $D_4$. Because device 800 may provide any desired distance between an initial (unexpanded) distance $D_i$ a final (fully expanded) distance $D_f$, advantageously the desired distance may be tailored to the patient without requiring additional components.

Receiving segment (not shown) of device 800 may be a screw in feature for attachment of device 800 to the distal end 50 of a penile implant 10 (similarly as shown in FIG. 1 for device 100 having receiving segment 400). For example, receiving segment 940 may be coupled to a distal end of the penile implant. The receiving segment is configured to rotatably receive the threaded portion 940 having plurality of threads 950 to secure the support segment 900 to the penile implant 10.

Support segment 900 may be of one-piece construction. Support segment 900 or any portion thereof, including tip portion 920, threaded portion 940, and expandable bellows segment 960, of the device 800 may include any suitable medical grade material. Examples of such materials include various biopolymer, and/or other various biologically compatible materials. In preferred instances, the biopolymer material is hydrophilic. In certain instances, the support segment 900 may be Bioflex®. In certain instances, the tip portion 920 may be a Bioflex®. In certain instances, the threaded portion 940 may be a Bioflex. In certain instances, the expandable bellows segment 960 may be a Bioflex. In some embodiments, the rounded tip portion 920 includes a shape contoured according to the distal end of the penile implant. In some embodiments, the tip portion 920 may be solid and substantially encircling port 980.

As the terms are used herein with respect to ranges of measurements (such as those disclosed immediately above), "about" and "approximately" may be used, interchangeably, to refer to a measurement, position, or arrangement, that includes the stated measurement, position, or arrangement and that also includes any measurement, positions, or arrangements that are reasonably close to the stated measurement, position, or arrangement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, positions, or arrangements, adjustments made to optimize performance and/or structural parameters in view of differences in measurements, positions, or arrangements associated with other components, particular implementation scenarios, imprecise adjustment and/or manipulation of objects by a person or machine, and/or the like.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A device for extending a penile implant, the device comprising:
   a support segment having a tip portion and a threaded portion;
   a receiving segment coupled to a distal end of the penile implant, the receiving segment configured to rotatably receive the threaded portion to secure the support segment to the penile implant; and
   at least one extension segment configured to at least partially surround the threaded portion to extend a length between the tip portion and the penile implant.

2. The device of claim 1, wherein the at least one extension segment comprises a plurality of extension segments.

3. The device of claim 2, wherein the plurality of extension segments includes a first extension segment of a first length and a second extension segment of a second length, wherein the first length is different from the second length.

4. The device of claim 3, wherein the first extension segment is arranged at the distal end of penile implant and the second extension segment is arranged between the first extension segment and the tip portion.

5. The device of claim 2, wherein the plurality of extension segments includes three extension segments configured to at least partially surround the threaded portion.

6. The device of claim 1, wherein the tip portion includes a rounded shape contoured according to the distal end of the penile implant.

7. The device of claim 1, wherein the support segment comprises a biopolymer material.

8. The device of claim 1, wherein the at least one extension segment comprises a biopolymer material.

9. The device of claim 1, wherein the receiving segment comprises a biopolymer material.

10. The device of claim 1, wherein the at least one extension segment is substantially cylindrical.

* * * * *